United States Patent [19]

Schulz, Jr. et al.

[11] Patent Number: 4,824,981
[45] Date of Patent: Apr. 25, 1989

[54] PROCESS TO PRODUCE SILYL KETENE ACETALS

[75] Inventors: William J. Schulz, Jr.; William H. Campbell, both of Midland, Mich.

[73] Assignee: Dow Corning Corporation, Midland, Mich.

[21] Appl. No.: 69,750

[22] Filed: Jul. 6, 1987

[51] Int. Cl.$^4$ .............................. C07F 7/08; C07F 7/18
[52] U.S. Cl. ...................................... 556/443; 556/446
[58] Field of Search ................................. 556/443, 446

[56] References Cited

U.S. PATENT DOCUMENTS

| | | | |
|---|---|---|---|
| 4,414,372 | 11/1983 | Farnham et al. | 526/190 |
| 4,417,034 | 11/1983 | Webster | 526/190 |
| 4,482,729 | 11/1984 | Ishikawa | 556/446 |
| 4,508,880 | 4/1985 | Webster | 526/190 |
| 4,577,041 | 3/1986 | Arai et al. | 556/446 |
| 4,746,750 | 5/1988 | Revis | 556/443 |

FOREIGN PATENT DOCUMENTS 0184692 6/1986 European Pat. Off. ..... 556/443 U X

OTHER PUBLICATIONS

Petrov et al., J. Gen. Chem. (USSR), 29 (1959), pp. 2896–2899.
Ainsworth et al., *J. Organometallic Chem.* 46 (1972), pp. 59–71.
Kita et al., *Tetrahedron Letters*, 24:12 (1983), pp. 1273–1276.
Brown, J. Org. Chem., 39:9 (1974), pp. 1324–1325.
Kuo et al., Chemical Communications, (1971), pp. 136–137.
Ojima et al., *J. Organometallic Chem.*, 111 (1976), pp. 43–60.
Howe et al., *J. Organometallic Chem.*, 208 (1981), pp. 401–406.
Yoshii et al., *Chem. Pharm. Bull.*, 22 (1974), pp. 2767–2769.
Chen et al., *J. Am. Chem. Soc.*, 94:11(1972), pp. 4037–4038.

*Primary Examiner*—Paul F. Shaver
*Attorney, Agent, or Firm*—James E. Bittell

[57] ABSTRACT

A process for the preparation of silyl ketene acetals of the formulae, $R^1R^2C=C(OR^3)OSiR_3^4$ and $R^1R^2C=C[OSiR_3^4]_2$, from the reaction of a malonate compound with a triorganohalosilane in the presence of an alkali metal. The malonate compounds are dialkyl dialkylmalonates, bis(trialkylsilyl) dialkylmalonates, and dialkylmalonic acids. The triorganohalosilane is present in stoichiometric excess relative to the malonate compounds. Silyl ketene acetals are isolated and separated.

22 Claims, No Drawings

PROCESS TO PRODUCE SILYL KETENE ACETALS

BACKGROUND OF THE INVENTION

This invention relates to a process for the manufacture of silyl ketene acetals. More specifically, this invention relates to a means of producing high-purity silyl ketene acetals from the reaction of dialkyl dialkylmalonates or bis(trialkylsilyl) dialkylmalonates and triorganohalosilanes in the presence of an alkali metal.

The first reference to preparation of silyl ketene acetals (SKA) was in the late-1950's by Petrov et al., *J. Gen. Chem. (USSR)*, 29(1959), pp. 2896-2899. This reference and most of the other references to the art deal with chemical species of the general formula,

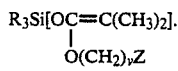

These organosilane intermediates are of value because of the ability to further react the SKA to prepare organic compounds which would be difficult to synthesize by other means. A very recent application is the use of the SKA as acrylate polymerization initiators. This concept known as Group Transfer Polymerization (GTP) was developed by DuPont and is disclosed in three U.S. patents—U.S. Pat. No. 4,414,372, Farnham et al., issued Nov. 8, 1983; U.S. Pat. No. 4,417,034, Webster, issued Nov. 22, 1983; and U.S. Pat. No. 4,508,880, Webster, issued Apr. 2, 1985.

Four procedures for preparing silyl ketene acetals are known in the art. The first general route to SKA is the reaction of an ester of a carboxylic acid with an appropriate metal reagent to form a metal enolate ion and subsequent reaction of the enolate ion with an organochlorosilane. Ainsworth et al., *J. Organometallic Chem.*, 46(1972), pp. 59-71, describe the preparation of an SKA via the reaction of esters of carboxylic acids with lithium diisopropylamide, followed by reaction with trimethylchlorosilane. Kita et al., *Tetrahedron Letters*, 24:12 (1983), pp. 1273-1276, discloses a similar procedure to prepare bifunctional SKA. Brown, *J. Org. Chem.*, 39:9(1974), pp. 1324-1325, describes the preparation of metal enolate ions by reacting potassium hydride in tetrahydrofuran with a carbonyl compound, followed by reaction with excess triethylamine and trimethylchlorosilane.

Kuo et al., *Chemical Communications*, (1971), pp. 136-137, discloses the preparation of silyl ketene acetals of the formula,

wherein $R^1$ and $R^2$ are hydrogen, methyl, t-butyl, and phenyl. The silyl ketene acetal is prepared by the reaction of the corresponding carboxylic acid or silyl ester of a carboxylic acid in contact with lithium diisopropylamide, trimethylchlorosilane, and tetrahydrofuran. Yields of the desired silyl ketene acetal of from 29 to 85 percent are disclosed. Kuo et al., are silent as to whether or not the yield figures disclosed are calculated by analysis or physical isolation and separation.

In a second general procedure, silyl ketene acetals are prepared by the hydrosilation of esters of carboxylic acid with organohydrosilanes. Petrov et al., *J. Gen. Chem. (USSR)*, 29(1959), pp. 2896-2899, described the platinum-catalyzed reaction of methyl methacrylate with triethylsilane. Ojima et al., *J. Organometallic Chem.*, 111(1976), pp. 43-60, studied the use of tris(triophenylphosphine)rhodium chloride as a catalyst. Howe et al., *J. Organometallic Chem.*, 208(1981), pp. 401-406, and Yoshii et al., *Chem. Pharm. Bull.*, 22(1974), pp. 2767-2769, describe yields of 70-75% SKA from the reaction of $(C_2H_5)_3SiH$ and methyl methacrylate using organophosphorous complexes of rhodium as a catalyst. Quirk et al., in European Patent Application 0184692, published June 18, 1986, discloses o-silylated ketene acetals and enol ethers and a process for their preparation from the reaction of acrylate esters and silanes or siloxanes in the presence of a rhodium catalyst.

In a third procedure Ishikawa et al., in U.S. Pat. No. 4,482,729, issued Nov. 13, 1984, describe the preparation of a fluoroalkyl silyl ketene acetal by the reaction of a fluorinated carboxylic acid ester with trimethylsilyl trifluoromethanesulfonate.

The fourth procedure involves the alkali metal reduction of disubstituted malonates in the presence of trimethylchlorosilane to produce a silyl ketene acetal. Kuo et al., *Chemical Communications*, (1971), pp. 136-137; and *J. Am. Chem. Soc.*, 94: 11 (1972), pp. 4037-4038, disclose the preparation of silyl ketene acetals of the formula,

from the reaction of a dialkyl dialkylmalonate with trimethylchlorosilane in the presence of sodium metal, wherein the $R^1$ and $R^2$ are methyl, ethyl, or phenyl; and $R^3$ is methyl or ethyl. The use of xylene and ammonia as solvents is disclosed by Kuo et al. Further, Kuo et al., discloses that the course of the reaction is different when xylene is used as a solvent as compared to the case when liquid ammonia is present. This result reported by Kuo et al., indicates that this reaction is solvent dependent. Nowhere does Kuo et al., disclose that silyl ketene acetals of the formula,

can be prepared from malonates.

SUMMARY OF THE INVENTION

The objectives of the instant invention are to provide an effective process for the preparation of silyl ketene acetals from malonate compounds. The reaction of disubstituted malonates with triorganohalosilanes in the presence of an alkali metal, as disclosed in the instant specification, has several advantages over those processes presently disclosed in the prior art. To begin with, many di-substituted malonates are commercially available. Further bis(silyl) dialkylmalonates may be easily synthesized from available raw materials.

Comparing the instant invention to the route in which SKA is prepared by the reaction of an ester of a carboxylic acid with an appropriate metal reagent to form a metal enolate ion and subsequent reaction of the enolate ion with an organochlorosilane, the instant invention has the advantage of lower raw material costs. The art teaches the preparation of metal enolate ions via the reaction of a carbonyl compound with a metallic reagent such as diisopropylamide or potassium hydride. Both of these metallic reagents are much more costly than the alkali metal utilized in the instant invention. The reactions can also include additional reagents such as triethylamine. The necessity for the additional reagents further adds to manufacturing cost.

The instant invention has advantages when compared to the route of preparing SKA by the hyrosilation of a vinylic material, such as methacrylate. Organosilanes, such as triorganosilanes, are not readily available in commercial quantities. A process must be established to prepare these triorganosilanes. Additionally, the starting vinylic materials are very susceptible to polymerization, and special precautions must be made to prevent vinylic polymerization during the preparation and separation of the desired SKA. Further, a by-product of the hydrosilation reaction is the the carbonyl adduct, $$CH_2=CR^1CH(OR^3)[OSi(CH_3)_3].$$

The carbonyl adduct is detrimental to the use wof the SKA as an acrylate polymerization initiator, supra. The preparation of SKA via hydrosilation requires special processing steps to remove these undesirable carbonyl adducts.

Several unexpected results are noted in the instant invention. It was found that both silyl ketene acetals of the formulae, $$R^1R^2C=C(OR^3)[OSi(CH_3)_3] \text{ and}$$

$$R^1R^2C=C[OSi(CH_3)_3]_2,$$

could be produced via the alkali-metal reduction of a disubstituted malonate. It was further found that trimethylchlorosilane serves effectively as both a solvent and a reactant to produce either the silyl ketene acetals. Additionally, it was found that an excess over the stoichiometric amount of an alkali metal assures complete reaction of a dialkylmalonate and maximizes the yield of the desired silyl ketene acetal. Finally, it was found that the form of the alkali metal was also a significant factor in the reactivity of the reaction system. All of these above findings were neither suggested nor demonstrated by the prior art, supra. The details of these findings will be illustrated in the examples, infra.

DESCRIPTION OF THE INVENTION

In accordance with the instant invention there is provided a process for the preparation of silyl ketene acetals from malonate compounds under conditions that will be delineated herein. What is described, therefore, is a process for preparing silyl ketene acetals having the general formula, $$R^i_2C=COSiR^{ii}_3,$$
$$\phantom{R^i_2C=C}|$$
$$\phantom{R^i_2C=C}OZ$$

wherein each $R^i$ and each $R^{ii}$ is independently selected from a group consisting of alkyl groups containing 1 to 4 carbon atoms, and wherein Z is selected from a group consisting of alkyl groups containing 1 to 4 carbon atoms and tiorganosilyl groups, said triorganosilyl groups having the formula, $$-SiR^{ii}_3,$$

said process comprising (A) contacting a malonate compound with a triorganohalosilane and an alkali metal, wherein the triorganohalosilane is present in a stoichiometric excess relative to the malonate compound, wherein said malonate compound is selected from a group consisting of (i) a dialkyl dialkylmalonate having the formula, $$R^i_2C(COR^i)_2,$$

(ii) a bis(trialkylsilyl) dialkylmalonate having the formula, $$R^i_2C(COSiR^{ii}_3)_2,$$

(iii) a dialkylmalonic acid having the formula, $$R^i_2C(COH)_2,$$

said triorganohalosilane having the general formula, $$R^i_3SiX,$$

wherein X is fluorine, chlorine, bromine, or iodine;
(B) separating and isolating the silyl ketene acetal.

The reaction of a dialkyl dialkylmalonate with a triorganohalosilane in the presence of an alkali metal generates the desired silyl ketene acetal, carbon monoxide, a triorganoalkoxysilane, and an alkali halide salt. Similarly the reaction of a bis(trialkylsilyl) dialkylmalonate with a triorganohalosilane in the presence of an alkali metal generates the desired silyl ketene acetal, carbon monoxide, a hexaorgaodisiloxane, and an alkali halide salt. The reaction of a dialkylmalonic acid and a triorganohalosilane forms a bis(trialkylsilyl) dialkylmalonate and generates a hydrogen halide.

The dialkyl dialkylmalonate may be, for example, dimethyl dimethylmalonate, dimethyl diethylmalonate, diethyl dimethylmalonate, diethyl diethylmalonate, methylethyl dimethylmalonate, or methylethyl diethylmalonate. The silyl ketene acetals prepared from the dialkyl dialkylmalonates may be, for example, $$(CH_3)(CH_3)C=COSi(CH_3)_3,$$
$$\phantom{(CH_3)(CH_3)C=C}|$$
$$\phantom{(CH_3)(CH_3)C=C}OCH_3$$

$$(C_2H_5)(C_2H_5)C=COSi(CH_3)_3,$$
$$\phantom{(C_2H_5)(C_2H_5)C=C}|$$
$$\phantom{(C_2H_5)(C_2H_5)C=C}OCH_3$$

$$(CH_3)(CH_3)C=COSi(CH_3)_3,$$
$$\phantom{(CH_3)(CH_3)C=C}|$$
$$\phantom{(CH_3)(CH_3)C=C}OC_2H_5$$

$$(C_2H_5)(C_2H_5)C=COSi(CH_3)_3,$$
$$\phantom{(C_2H_5)(C_2H_5)C=C}|$$
$$\phantom{(C_2H_5)(C_2H_5)C=C}OC_2H_5$$

$$(CH_3)(C_2H_5)C=COSi(CH_3)_3,$$
$$\phantom{(CH_3)(C_2H_5)C=C}|$$
$$\phantom{(CH_3)(C_2H_5)C=C}OCH_3$$

or $$(CH_3)(C_2H_5)C=COSi(CH_3)_3.$$
$$\phantom{(CH_3)(C_2H_5)C=C}|$$
$$\phantom{(CH_3)(C_2H_5)C=C}OC_2H_5$$

The bis(trialkylsilyl) dialkylmalonate may be, for example, bis(trimethylsilyl) dimethylmalonate,

or bis(trimethylsilyl) diethylamalonate,

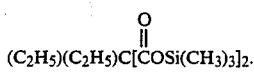

The silyl ketene acetals prepared from the bis(trialkylsilyl) dialkylmalonate may be, for example,

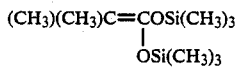

or

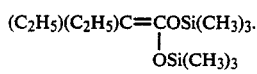

The dialkylmalonic acid may be, for example, dimethylmalonic acid, diethylmalonic acid, or dibutylmalonic acid.

The triorganohalosilane may be, for example, trimethylchlorosilane, trimethylbromosilane, trimethyliodosilane, or triethylchlorosilane.

The alkali metal may be lithium, sodium, potassium, or cesium. The preferred alkali metals are sodium and potassium. The alkali metal may be used in the form of an alloy of two or more of the metals, such as a sodium/potassium alloy. The alkali metal may also be used in the form of a dispersion in an appropriate hydrocarbon solvent such as a paraffin. The form of the alkali metal has a significant effect upon the reaction of a bis(trialkylsilyl) dialkylmalonate with a triorganohalosilane and an alkali metal, as noted in the examples infra.

In the preparation of silyl ketene acetals from either dialkyl dialkylmalonates or bis(trialkylsilyl) dialkylmalonates, contacting the malonate compound with the triorganohalosilane and the alkali metal comprises (C) mixing the triorganohalosilane with the alkali metal;

(D) adding the malonate compound to the mixture of the triorganohalosilane and the alkali metal; and (E) facilitating reaction among the malonate compound, the triorganohalosilane, and the alkali metal to form the silyl ketene acetal.

Mixing the triorganohalosilane with the alkali metal can be carried out in a standard batch chemical reactor system. The reactor should be provided with adequate means for agitation to assure that the alkali metal is dispersed in the liquid reaction medium. The chemical reactor should also have provisions such as pumps, weigh tanks, or the like for adding malonate compounds to the agitated mixture of solid alkali metal particles and liquid reactants. For the purposes of the instant invention "facilitating reaction" means that the reactor should have provisions such as adequate agitation, heating and cooling, as necessary, adequate liquid content to assure that the slurry formed by the liquid reactants and products and solid alkali salts is a manageable physical mixture, and provisions for safely venting and disposing of carbon monoxide.

In the preparation of silyl ketene acetals, starting with a dialkylmalonic acid, contacting of this malonate compound further involves the steps of (K) mixing a first portion of the triorganohalosilane with the dialkylmalonic acid;

(L) facilitating reaction of the mixture from (K) to form a bis(trialkylsilyl) dialkylmalonate, said bis(trialkylsilyl) dialkylmalonate having the formula,

(M) separating and isolating the bis(trialkylsilyl) dialkylmalonate formed in (L);

(N) mixing a second portion of the triorganohalosilane with the alkali metal;

(P) adding the bis(trialkylsilyl) dialkylmalonate to the mixture of the second portion of the triorganohalosilane and the alkali metal; and (Q) facilitating reaction among the bis(trimethylsilyl) dialkylmalonate, the triorganohalosilane, and the alkali metal to form the silyl ketene acetal.

Alternatively, the bis(trialkylsilyl) dialkylmalonate is not isolated and separated; and, as such, contacting the malonate compound with the triorganohalosilane and the alkali metal comprises (F) mixing the triorganohalosilane with the dialkylmalonic acid;

(G) facilitating reaction of the triorganohalosilane and the dialkylmalonic acid from (F) to form a bis(trialkylsilyl) dialkylmalonate;

(H) adding the alkali metal to the mixture from (G); and (J) facilitating reaction among the bis(trialkylsilyl) dialkylmalonate, the triorganohalosilane, and the alkali metal to form the silyl ketene acetal.

The provisions for mixing and "facilitating reaction" have essentially been described, supra. Additional provisions needed to facilitate reaction between the triorganohalosilane and the dialkylmalonic acid are provisions for the handling of hydrogen halide. These provisions may include facilities for venting the gases, as they are formed, from the reactor—facilities such as pressure control or a sweep of inert gas. Additionally, these provisions should include means for recovering or disposing of the hydrogen halide—provisions such as a water scrubber. Separating and isolating the bis(trialkylsilyl) dialkylmalonate can be effected by such known processes as distillation.

In the preparation of silyl ketene acetals in which the starting malonate compound is either a dialkyl dialkylmalonate or a bis(trialkylsilyl) dialkylmalonate, the stoichiometric amount of the triorganohalosilane relative to the malonate compound is 2.0:1. For purposes of the instant invention the term "stoichiometric excess relative to the malonate compound" means a molar ratio greater than the stoichiometric amount. To assure complete reaction among the malonate compound, the alkali metal, and the triorganohalosilane and to assure sufficient dilution of the reactant slurry, the molar ratio of the triorganohalosilane relative to the malonate compound should be greater than about 3.0:1, a stoichiometric excess of greater than about 50 percent. Preferably this molar ratio should be greater than about 5.0:1, a stoichiometric excess of greater than about 150 percent. More preferably, this stoichiometric excess should be in a range of from about 50 to 150 percent.

For the preparation of silyl ketene acetals in which the starting malonate compound is a dialkylmalonic acid, the stoichiometric amount of triorganohalosilane needed is 2.0 moles for the reaction of the triorganohalosilane with 1.0 mole dialkylmalonic acid to form the bis(trialkylsilyl) dialkylmalonate. Additionally, 2.0 moles of triorganohalosilane are needed for the subsequent reaction with 1.0 mole bis(trialkylsilyl) dialkylmalonate. To assure complete reaction among the dialkylmalonate, the alkali metal, and the dialkylmalonate, the molar ratio of the triorganohalosilane relative to the dialkyl malonic acid should be greater than about 5.0:1, a stoichiometric excess of greater than about 150 percent. Preferably this molar ratio should be greater than about 7.0:1, a stoichiometric excess of greater than about 250 percent. More preferably this stoichiometric excess should be in a range from about 150 to 250 percent.

The stoichiometric excess of triorganohalosilane relative to the malonate compound is needed to assure rapid and complete reaction. The excess triorganohalosilane also serves as a solvent to assure that the liquid-solid reaction slurry is fluid enough to facilitate agitation and movement of the reaction mixture for subsequent processing. Molar excesses of the triorganohalosilane greater than those disclosed above may be utilized; however, the inventor believes that no further benefit will be realized in the use of such excesses.

The inventor of the instant invention has found that a stoichiometric excess of the alkali metal relative to the malonate material has a significant impact upon the completeness of reaction to form the desired SKA. This effect is demonstrated in the examples, infra. The stoichiometric amount of the alkali metal relative to the dialkyl dialkylmalonate or bis(trialkylsilyl) dialkylmalonate is 2.0:1. The inventor believes that a stoichiometric excess as low as 5 percent or 2.10:1 is sufficient to maximize the completeness of reaction. However, to assure that this effect is consistently realized, a stoichiometric excess of the alkali metal greater than about 10 percent relative to the malonate material is preferred. A stoichiometric excess of the alkali metal in the range of about 10 to 25 percent is more preferred. A stoichiometric excess of the alkali metal greater than 25 percent may be utilized; however, no added advantage is apparent. Conversely, less than the stoichiometric amount of alkali metal may be utilized; however, this will result in less completeness of the reaction.

In the preparation of SKA from the reaction of a dialkyl dialkylmalonate with excesses of both the triorganohalosilane and the alkali metal, as described supra, the reaction mixture heats sponaneously to the reflux or boiling temperature of the trioganohalosilane; the reaction mixture subsequently cools after several hours. In this manner, starting at a temperature of about 25° C., the reaction is complete within 20 hours. The reaction is often essentially complete in as little as 2 hours. Higher temperatures will reduce the needed reaction time even further.

For the reaction of a bis(trialkylsilyl) dialkylmalonate with excesses of both the triorganohalosilane and the alkali metal higher temperatures appear to be needed to effect the reaction is a reasonable length of time. The inventor has found that the reaction is essentially complete after 20 hours at a temperature of greater than about 50° C. when the alkali metal is in a reactive form such as a dispersion in a paraffin (as described in the examples, infra). The reaction is often essentially complete in as short a time as 2 to 10 hours at a temperature of about 50° C.

Separating and isolating the silyl ketene acetal comprises
(Q) removing alkali halide solids; and
(R) recovering the silyl ketene acetal by distillation.
Solid alkali metal halides are a product of the reaction to produce the desired SKA. These salts are generated at a volume of 2 moles per mole of SKA. These salts may be removed by such known techniques as filtration of the salts from the crude reaction mixture. Any commercial filtration method such as pressure filtration can be utilized.

Recovery of the desired SKA from the solids-free crude reaction mixture can be effected by such known techniques as distillation. It has been shown in the examples, infra, that SKA prepared by the process of the instant invention can be recovered by distillation to purities of at least 95 weight percent.

So that those skilled in the art may better understand the instant invention, the following examples are presented. The examples are presented as being illustrative and are not to be construed as limiting the instant invention as delineated in the claims.

EXAMPLE 1

A silyl ketene acetal (SKA) was prepared from the reaction of a dialkyl dialkylmalonate with trimethylchlorosilane in the presence of sodium metal. The procedures followed in this preparation are typical of subsequent examples of preparation of an SKA from a dialkyl dialkylmalonate.

Into a 5000-milliliter (ml), three-necked laboratory flask, fitted with a mechanical agitator and a reflux condenser, was added 2512 grams (g) (23.1 moles) of trimethylchlorosilane. To the reaction flask as added 266 g (11.6 moles) of sodium metal cut into 2 g pieces. The mixture in the flask was agitated and the system was placed under a nitrogen purge. 1000 g (4.62 moles) of diethyl diethylmalonate were added to an addition funnel that was attached to the reaction flask. The trimethylchlorosilane, sodium metal, and diethyl diethylmalonate are commercially available materials.

The diethyl diethylmalonate was added to the flask at a rate of about 30 ml/minute. The total addition time was approximately 30 minutes. The reaction began spontaneously with significant evolution of heat. About 15 minutes into the addition of the malonate material rapid evolution of carbon monoxide gas began. The reaction mixture refluxed spontaneously for about 3 hours after the malonate addition was completed. The system was held with agitation overnight under a nitrogen purge.

A sample of the mixture in the flask was taken and analyzed by gas chromatographic means: The analyses indicated that the reaction was essentially complete. Based upon the malonate-type materials present (excluding excess trimethylchlorosilane, trimethylethoxysilane, and other non-malonate materials) the crude reaction liquid had an analysis of 94.0 percent (gas chromatographic area percent) of the desired SKA,

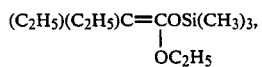

2.2 percent diethyl diethylmalonate, and 1.7 percent ethyl 2-ethylbutyrate,

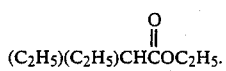

The mixture was then filtered by standard reduced pressure filtration through a fritted filter medium to remove the sodium chloride and unreacted sodium metal. The filtered solids were washed with trimethylchlorisilane. The resulting filtrate and wash liquid were combined, and the volatiles were removed under reduced pressure. The devolatilized material was then distilled at reduced pressure in a laboratory distillation apparatus. The temperature of the overhead product during distillation was maintained at 67° to 68° C. at a pressure of 8 mm Hg. A total of 936 grams of product was taken overhead. A cut of 734 g was taken and was found by gas chromatography to be greater than 98 percent of the desired silyl ketene acetal.

The above results demonstrate that silyl ketene acetals can be produced in high yield from the reaction of a dialkyl dialkylmalonate with a trialkylhalosilane in the presence of sodium metal, excess of the trialkylhalosilane being used as a solvent or diluent for the reaction mixture, the sodium metal being present in an excess of the stoichiometric amount.

EXAMPLE 2

Several runs were made to produce the silyl ketene acetal,

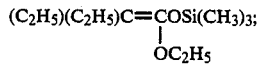

from the reaction of diethyl diethylmalonate with trimethylchlorosilane in the presence of sodium metal. Procedures and analyses are similar to those used in Example 1.

As in Example 1, sodium metal in small chucks (in most cases, 0.1 to 0.5 g pieces) were added to the trimethylchlorosilane at a temperature of approximately 25° C. The temperature of 25° C. represents the starting temperature. Upon addition of the malonate material, the reaction mixture heated spontaneously and then cooled as the run progressed. In one case, the reaction flask was heated to reflux at approximately 58° C. before addition of the malonate material.

The diethyl diethylmalonate was added over a period of about 1 to 5 minutes. The flask was held at the desired temperature for 20 hours in all runs. The liquid mixture was sampled after 20 hours and analyzed by a gas chromatographic technique. As in Example 1, the results reported exclude excess trimethylchlorosilane and by-product trimethylethoxysilane.

Table 1 is a summary of the results of the five runs in this series. These five runs are designated Samples A, B, C, D, and E, respectively. The runs are identified by (1) the molar ratio of sodium to diethyl diethylmalonate (2.0 being the stoichiometric ratio), the molar ratio being designated as "Equiv Na"; (2) the molar ratio of trimethylchlorosilane to diethyl diethylmalonate (2.0 being the stoichiometric ratio), the molar ratio being designated "Equiv Me₃"; (3) the starting temperature of the reaction flask (in °C.), designated as "Temp"; and (4) gas chromatographic analyses of the reaction liquid for the content of the SKA and unreacted diethyl diethylmalonate, designated as "%SKA" and "%Mal".

TABLE 1

| Sample | Equiv Na | Equiv Me₃ | Temp | % Mal | % SKA |
|---|---|---|---|---|---|
| A | 2.0 | 5.0 | 25 | 8.0 | 88.0 |
| B | 2.0 | 5.0 | 58 | 8.0 | 88.0 |
| C | 2.5 | 5.0 | 25 | 1.6 | 92.9 |
| D | 2.5 | 3.0 | 25 | 1.2 | 92.4 |
| E | 2.5 | 5.0 | 25 | 2.2 | 94.0 |

The above results demonstrate that silyl ketene acetal is effectively prepared in the presence of an excess of trimethylchlorosilane, with no other solvent present. Further, these results demonstrate that an excess of sodium over the stoichiometric quantity facilitates higher conversion of dialkyl dialkylmalonate to the desired SKA.

EXAMPLE 3

Runs were made to prepare silyl ketene acetals from the reaction of various dialkyl dialkylmalonate with trimethylchlorosilane in the presence of sodium metal. The SKA can be represented by the formula,

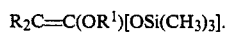

The corresponding dialkyl dialkylmalonates can be represented by the formula.

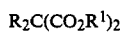

R and R¹ represent either a methyl group (Me) or an ethyl group (Et). These SKA and the starting dialkyl dialkylmalonates are listed in Table 2. The runs to produce these SKA are designated as Samples F, G, H, J, and K, respectively. In Table 2 the dialkyl dialkylmalonates are designated as "DADAM".

TABLE 2

| Sample | SKA | DADAM |
|---|---|---|
| F | Et₂C=C(OEt)[OSi(CH₃)₃] | Et₂C(CO₂Et)₂ |
| G | Me₂C=C(OEt)[OSi(CH₃)₃] | Me₂C(CO₂Et)₂ |
| H | Et₂C=C(OMe)[OSi(CH₃)₃] | Et₂C(CO₂Me)₂ |
| J | Me₂C=C(OMe)[OSi(CH₃)₃] | Me₂C(CO₂Me)₂ |
| K | Me₂C=C(OMe)[OSi(CH₃)₃] | Me₂C(CO₂Me)₂ |

The diethyl diethylmalonate, diethyl dimethylmalonate, and dimethyl diethylmalonate are commercially available chemical intermediates. Dimethyl dimethylmalonate is not presently a commercially available chemical intermediate.

The dimethyl dimethylmalonate was prepared from commercially available dimethyl malonate. The dimethyl malonate was alkylated via a known route in which the dimethyl malonate was added to a methanol solution of sodium methoxide. Excess methyl chloride was bubbled through the mixture. The alkylation took place in two steps, in which the dimethyl malonate was first converted to dimethyl methylmalonate and then subsequently further reacted with sodium methoxide and methyl chloride, as above, to form dimethyl dimethylmalonate. A crude mixture of malonate material that was approximately 95 percent dimethyl dimethylmalonate was formed. Sodium chloride was washed from the crude product with water. The dimethyl dimethylmalonate product was separated by distillation at reduced pressure, the dimethyl dimethylmalonate being distilled at an overhead temperature of 60° to 61° C. at a pressure of 8 mm Hg. The dimethyl dimethylmalonate so recovered had a purity of 99.8 percent by chromatographic analysis.

The above dialkyl dialkylmalonates were individually reacted with trimethylchlorosilane in the presence of sodium metal using the same procedures and analytical techniques as utilized in Example 2. Table 3 is a summary of the results of these runs. The notation in Table 3 is the same as utilized in Example 2.

TABLE 3

| Sample | Equiv Na | Equiv Me₃ | Temp | % Mal | % SKA |
|--------|----------|-----------|------|-------|-------|
| F | 2.5 | 3.0 | 25 | 1.2 | 92.4 |
| G | 2.5 | 5.0 | 25 | 2.6 | 91.2 |
| H | 2.25 | 5.0 | 25 | 1.2 | 90.2 |
| J | 2.25 | 5.0 | 25 | 2.0 | 95.2 |
| K | 2.25 | 5.0 | 25 | 3.2 | 93.5 |

The above results demonstrate the preparation of a series of silyl ketene acetals from corresponding dialkyl dialkylmalonates. The above results further demonstrate the benefits of the use of sodium metal at levels above the stoichiometric quantity. Finally the above results again demonstrate that silyl ketene acetals can be effectively produced by this route in which excess trimethylchlorosilane is utilized to eliminate the need for an additional solvent.

EXAMPLE 4

Silyl ketene acetal,

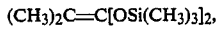
$(CH_3)_2C=C[OSi(CH_3)_3]_2$, was prepared via the reaction a bis(trialkylsilyl) dialkylmalonate,

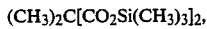
$(CH_3)_2C[CO_2Si(CH_3)_3]_2$, with trimethylchlorosilane in the presence of sodium metal.

The bis(trimethylsilyl) dimethylmalonate (BTMSDMM) was prepared from commercially available dimethylmalonic acid (DMA). 1 mole of DMA was reacted with slightly more than 2 moles of trimethylchlorosilane. The reaction mixture was heated to smoothly generate the desired BTMSDMM. By-product hydrogen chloride was vented from the reactor. The BTMSDMM was isolated and recovered by vacuum distillation. The BTMSDMM was recovered as an overhead product at an overhead temperature of 101° to 103° C. at 14 mm Hg. The BTMSDMM had a purity, as determined by gas chromatography, of greater than 99 percent.

The BTMSDMM was reacted with trimethylchlorosilane in the presence of sodium metal in a manner similar to the procedures used in Examples 2 and 3. Gas chromatography was utilized to analyze the crude product. 5.0 moles of trimethylchlorosilane and 2.25 moles sodium metal were used per mole of BTMSDMM. The reaction was allowed to proceed at room temperature for about 6 days. The crude product was analyzed by gas chromatography to contain 85.0 percent of the desired SKA and 3.1 percent unreacted BTMSDMM.

The above results demonstrate the preparation of a bis-silyl ketene acetal from the reaction of a bis(trialkylsilyl) dialkylmalonate with a triorganohalosilane in the presence of sodium metal.

EXAMPLE 5

The silyl ketene acetal,

$(CH_3)_2C=C[OSi(CH_3)_3]_2$, was then prepared in a "one-pot" method in which the BTMSDMM was not isolated. In this particular preparation, 7.0 moles of trimethylchlorosilane and 1.0 mole of dimethylmalonic acid were charged to a flask. The mixture was heated to reflux until all of the solid dimethylmalonic acid had disappeared. The mixture was then cooled to approximately 25° C. Next, 2.25 moles of sodium metal, as chucks, was added to the flask, and the total mixture was heated to reflux. The reaction proceeded with agitation for 8 days. At this point, the crude mixture was sampled and analyzed by gas chromatography. The crude product analysis was 92.3 percent SKA and 5.1 percent BTMSDMM. The by-product sodium chloride solids were separated by standard reduced pressure filtration. The filtered solids were washed with fresh trimethylchlorosilane. The desired SKA was isolated and recovered by vacuum distillation. The desired product was taken off at an overhead temperature of 115° to 117° C. at a pressure of 105 mm Hg. A fraction which represented approximately 62 weight percent of the overhead product was isolated and analyzed by gas chromatography to be greater than 98 percent of the desired SKA.

The above result demonstrates that a silyl ketene acetal can be produced via a procedure which starts with a dialkylmalonic acid in excess triorganohalosilane without the isolation and separate addition of a bis(-trialkylsilyl) dialkylmalonate.

EXAMPLE 6

Two runs were made to prepare

$(CH_3)_2C=C[OSi(CH_3)_3]_2$.

These runs were made to determine the impact of the form of sodium metal on the reaction of BTMSDMM and trimethylchlorosilane. These runs were made using the procedures and analytical techniques of Example 4.

In the first run, designated Sample M, the sodium metal was added as a 50 weight percent dispersion in a liquid paraffin. In the second run, designate Sample N, the sodium was introduced as as a 70:30 by weight alloy of sodium:potassium. The sodium dispersion in paraffin is commercially available. The sodium:potassium alloy was prepared by physically mixing the two metals via a procedure in which chucks of potassium metal were mixed with molten sodium under an argon atmosphere. In the case of the sodium dispersion in paraffin, the dispersion was added to the trimethylchlorosilane, and the BTMSMM was added to this mixture similarly to the procedure used in Example 4. In the case of the sodium:potassium alloy, the trimethylchlorosilane was added to the alloy very slowly. The BTMSMM was subsequently added to this mixture. In both runs, the amount of sodium metal is 2.25 moles per mole of BTMSDMM.

In both of the preparations, the sodium metal reacted very vigorously when added to the trimethylchlorosilane. The reaction mixtures were allowed to stand with agitation for about 20 hours before sampling and analyses. However, in the case of the sodium:potassium alloy, the inventor strongly believes from observing the behavior of the reaction mixture that the reaction was completed in a much shorter time—estimated at about 2 hours.

Table 4 is a summary of the results of these two runs. As a comparison, the run of Example 4 in which sodium metal was added as chunks is included and is designated as Sample L. Table 4 lists the results by (1) reaction time, designated as "Time"; (2) SKA content of the crude product, designated as "%SKA"; and (3) unreacted malonate content of crude product, designated as "%Mal".

TABLE 4

| Sample | Time | % SKA | % Mal |
|--------|---------|-------|-------|
| L | 6 days | 85.0 | 3.1 |
| M | 20 hours | 76.1 | 6.9 |
| N | 20 hours | 90.6 | 2.0 |

The above results demonstrate that the form in which the sodium metal is used has an impact on the rate of reaction of a bis(trialkylsilyl) dialkylmalonate with a triorganohalosilane.

What is claimed is:

1. A process for preparing silyl ketene acetals having the general formula, $$R_2^i C = C(OSiR_3^{ii})_2,$$

wherein each $R^i$ and each $R^{ii}$ is independently selected from a group consisting of alkyl groups containing 1 to 4 carbon atoms, said process comprising
(A) contacting a malonate compound with a triorganohalosilane and an alkali metal, wherein the triorganohalosilane is present in stoichiometric excess relative to the malonate compound, wherein said malonate compound is selected from a group consisting of
  (i) a bis(trialkylsilyl) dialkylmalonate having the formula, $$R_2^i C(\overset{O}{\overset{\|}{C}}OSiR_3^{ii})_2,$$

and
  (ii) a dialkylmalonic acid having the formula, $$R_2^i C(\overset{O}{\overset{\|}{C}}OH)_2,$$

said triorganohalosilane having the general formula $$R_3^{ii}SiX,$$

wherein X is fluorine, chlorine, bromine, or iodine;
(B) separating and isolating the silyl ketene acetal.

2. A process according to claim 1, wherein the malonate compound is a bis(trialkylsilyl) dialkylmalonate, wherein the silyl ketene acetal has the formula, $$R_2^i C = COSiR_3^{ii},$$
$$\quad |$$
$$\quad OSiR_3^{ii}$$

and wherein (A) contacting the malonate compound with the triorganohalosilane and the alkali metal comprises
  (C) mixing the triorgaohalosilane with the alkali metal;
  (D) adding the bis(trialkylsilyl) dialkylmalonate to the mixture of the triorganohalosilane and the alkali metal; and
  (E) facilitating reaction among the bis(trialkylsilyl) dialkylmalonate, the triorganohalosilane, and the alkali metal to form the silyl ketene acetal.

3. A process according to claim 1, wherein the malonate compound is dialkylmalonic acid, wherein the silyl ketene acetal has the formula, $$R_2^i C = COSiR_3^{ii},$$
$$\quad |$$
$$\quad OSiR_3^{ii}$$

and wherein (A) contacting malonate compound with the triorganohalosilane and the alkali metal comprises
  (F) mixing the triorganohalosilane with the dialkylmalonic acid;
  (G) facilitating reaction of the triorganohalosilane and the dialkylmalonic acid from (F) to form a bis(trialkylsilyl) dialkylmalonate;
  (H) adding the alkali metal to the mixture from (G); and
  (J) facilitating reaction among the bis(trialkylsilyl) dialkylmalonate, the triorganohalosilane, and the alkali metal to form the silyl ketene acetal.

4. A process according to claim 1, wherein the malonate compound is a dialkylmalonic acid, wherein the silyl ketene acetal has the general formula, $$R_2^i C = COSiOR_3^{ii},$$
$$\quad |$$
$$\quad OSiR_3^{ii}$$

and wherein (A) contacting malonate compound with the triorganohalosilane and the alkali metal comprises
  (K) mixing a first portion of the triorganohalosilane with the dialkylmalonic acid;
  (L) facilitating reaction of the mixture from (K) to form a bis(trialkylsilyl) dialkylmalonate, said bis(trialkylsilyl) dialkylmalonate having the formula, $$R_2^i C(\overset{O}{\overset{\|}{C}}OSiR_3^{ii})_2,$$

(M) separating and isolating the bis(trialkylsilyl) dialkylmalonate formed in (L);
  (N) mixing a second portion of the triorganohalosilane with the alkali metal;
  (P) adding the bis(trialkylsilyl) dialkylmalonate to the mixture of the second portion of the triorganohalosilane and the alkali metal; and
  (E) facilitating reaction among the bis(trimethylsilyl) dialkylmalonate, the triorganohalosilane, and the alkali metal to form the silyl ketene acetal.

5. A process according to claim 2, wherein the triorganohalosilane is present in a stoichiometric excess relative to the malonate compound of greater than about 50 percent.

6. A process according to claim 3, wherein the triorganohalosilane is present in a stoichiometric excess relative to the malonate compound of greater than about 150 percent.

7. A process according to claim 4, wherein the triorganohalosilane is present in a stoichiometric excess relative to the malonate compound of greater than about 150 percent.

8. A process according to claim 1, wherein the alkali metal is sodium.

9. A process according to claim 1, wherein the alkali metal is a sodium/potassium alloy.

10. A process according to claim 2, wherein the alkali metal is in the form of a dispersion in a hydrocarbon solvent.

11. A process according to claim 3, wherein the alkali metal is in the form of a dispersion in a hydrocarbon solvent.

12. A process according to claim 4, wherein the alkali metal is in the form of a dispersion in a hydrocarbon solvent.

13. A process according to claim 1, wherein separating and isolating the silyl ketene acetal comprises
   (Q) removing alkali halide solids; and
   (R) recovering the silyl ketene acetal by distillation.

14. A process according to claim 1, wherein the alkali metal is present in stoichiometric excess relative to the malonate compound.

15. A process according to claim 2, wherein the alkali metal is sodium, wherein the triorganohalosilane is trimethylchlorosilane, wherein the sodium is present in a stoichiometric excess of greater than about 5 percent and the trimethylchlorosilane is present at a stoichiometric excess of greater than about 50 percent, said stoichiometric excesses being relative to the bis(trialkylsilyl) dialkylmalonate; wherein starting contact temperature is greater than about 50°.; wherein contact time is at least two hours; wherein sodium chloride is removed by filtration; and wherein the silyl ketene acetal is separated and isolated by distillation.

16. A process according to claim 15, wherein the sodium is present in a stoichiometric excess in the range of about 10 to 25 percent; the trimethylchlorosilane is present in a stoichiometric excess in the range of about 50 to 150 percent; wherein the contact time is greater than about 10 hours; and wherein the silyl ketene acetal is separated and isolated at a purity greater than about 95 weight percent.

17. A process according to claim 16, wherein the bis(trialkylsilyl) dialkylmalonate is bis(trimethylsilyl) diethylmalonate,

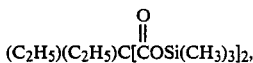

and wherein the silyl ketene acetal is

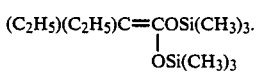

18. A process according to claim 16, wherein the bis(trialkylsilyl) dialkylmalonate is bis(trimethylsilyl) dimethylmalonate,

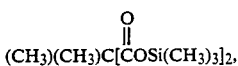

and the silyl ketene acetal is

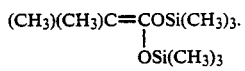

19. A process according to claim 3, wherein the triorganohalosilane is trimethylchlorosilane; wherein the alkali metal is sodium; wherein the trimethylchlorosilane is present in a stoichiometric excess of greater than about 150 percent relative to the dialkylmalonic acid; wherein starting contact temperature between the dialkylmalonic acid and trimethylchlorosilane is greater than about 50° C.; wherein the sodium is percent in a stoichiometric excess of greater than about 5 percent relative to the bis(trialkylsilyl) dialkylmalonate; wherein the starting contact temperature among the tris(trialkylsilyl) dialkylmalonate, the trimethylchlorosilane, and the sodium is greater than about 50° C.; wherein contact time is at least two hours; wherein sodium chloride is removed by filtration; and wherein the silyl ketene acetal is separated and isolated by distillation.

20. A process according to claim 19, wherein the sodium is present in a stoichiometric excess in the range of about 10 to 25 percent; wherein in the trimethylchlorosilane is present in a stoichiometric excess in the range of about 150 to 250 percent; wherein the contact time is greater than about 20 hours; and wherein the silyl ketene acetal is separated and isolated at a purity greater than about 95 weight percent.

21. A process according to claim 20, wherein the dialkylmalonic acid is dimethylmalonic acid; wherein the bis(trialkylsilyl) dialkylmalonate is bis(trimethylsilyl) dimethylmalonate,

and wherein the silyl ketene acetal is

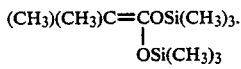

22. A process according to claim 20, wherein the dialkylmalonic acid is diethylmalonic acid, wherein the bis(trialkylsilyl) dialkylmalonate is bis(trimethylsilyl) diethylmalonate,

and wherein the silyl ketene acetal is

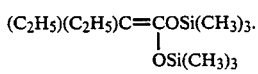

* * * * *